(12) United States Patent
Kincaid et al.

(10) Patent No.: US 11,950,552 B2
(45) Date of Patent: Apr. 9, 2024

(54) APPARATUS FOR AUTOMATED CONTROL FOR A PERFORMANCE VEGETATION WALL SYSTEM

(71) Applicant: RK SAGE, LLC, Northbrook, IL (US)

(72) Inventors: Richard Kincaid, Northbrook, IL (US);
Harry Eschel, Wilmette, IL (US);
Ronaldo J. Santiago, South Elgin, IL (US)

(73) Assignee: RK SAGE, LLC, Northbrook, IL (US)

( * ) Notice: Subject to any disclaimer, the term of this patent is extended or adjusted under 35 U.S.C. 154(b) by 0 days.

(21) Appl. No.: 18/186,498

(22) Filed: Mar. 20, 2023

(65) Prior Publication Data

US 2023/0225259 A1    Jul. 20, 2023

Related U.S. Application Data

(62) Division of application No. 16/661,928, filed on Oct. 23, 2019, now Pat. No. 11,606,915.

(60) Provisional application No. 62/749,827, filed on Oct. 24, 2018.

(51) Int. Cl.
| | |
|---|---|
| *A01G 9/24* | (2006.01) |
| *A01G 7/04* | (2006.01) |
| *A01G 9/02* | (2018.01) |
| *A01G 27/00* | (2006.01) |
| *G01N 33/00* | (2006.01) |
| *H04W 84/18* | (2009.01) |

(52) U.S. Cl.
CPC ............... *A01G 9/24* (2013.01); *A01G 7/045* (2013.01); *A01G 9/023* (2013.01); *A01G 9/247* (2013.01); *A01G 9/249* (2019.05); *A01G 27/001* (2013.01); *A01G 27/003* (2013.01); *G01N 33/0098* (2013.01); *H04W 84/18* (2013.01)

(58) Field of Classification Search
CPC .......... A01G 9/24; A01G 9/26; A01G 27/001; A01G 27/003
See application file for complete search history.

(56) References Cited

U.S. PATENT DOCUMENTS

| | | | | |
|---|---|---|---|---|
| 10,021,838 B1 * | 7/2018 | Gustafik | ................. | G05B 15/02 |
| 2011/0238226 A1 * | 9/2011 | Schmidt | ............... | A01G 27/003 700/284 |
| 2015/0070188 A1 * | 3/2015 | Aramburu | ............ | A01G 25/167 340/870.02 |

* cited by examiner

*Primary Examiner* — Peter M Poon
*Assistant Examiner* — Shada Mohamed Alghailani
(74) *Attorney, Agent, or Firm* — William J. Clemens; Shumaker, Loop & Kendrick, LLP

(57) ABSTRACT

A vegetation wall system includes an irrigation tank, a vegetation mounting unit with a vegetation holding unit, a pump feeding water from the tank to the holding unit, a programmable logic control unit including a central processing unit and a sensor, wherein the central processing unit monitors an aspect in the wall system by measuring, by the sensor, a component of the aspect as a first component measurement, waiting a predetermined period of time and then measuring, by the sensor, the component of the aspect as a second component measurement, determining, by the central processing unit, a change in the aspect based on the first and second measurements and the predetermined period of time, determining whether the change is outside a threshold range, in response to determining that the change is outside the threshold range, determining that an anomalous condition exists, and generating an alert when the anomalous condition exists.

6 Claims, 9 Drawing Sheets

APPARATUS FOR AUTOMATED CONTROL FOR A PERFORMANCE VEGETATION WALL SYSTEM

CROSS-REFERENCE TO RELATED APPLICATIONS

This application is a divisional of the U.S. patent application Ser. No. 16/661,928, filed Oct. 23, 2019, and to be issued on Mar. 21, 2023 as U.S. Pat. No. 11,606,915.

The present patent application is related to and claims the priority benefit of U.S. Provisional Patent Application Ser. No. 62/749,827, filed Oct. 24, 2018, the content of which is hereby incorporated by reference in its entirety into this disclosure.

FIELD OF THE INVENTION

This invention relates to vegetation wall systems. More particularly, the invention is directed to a vegetation wall system capable of monitoring at least one aspect of the system for anomalous conditions.

BACKGROUND OF THE INVENTION

This section provides background information related to the present disclosure which is not necessarily prior art.

Built environments, such as commercial buildings, offices, retail stores, factories, urban infrastructure, and homes, have effects on the wellbeing, productivity and mood of its occupants. Adding plants and light to built environments can greatly improve the wellbeing, profitability, work productivity and air quality of their occupants. Plants provide cleaner air by absorbing carbon dioxide in the surrounding environment. However, the disbursement of plants requires maintenance. To survive, plants require adequate heat, light, water, and fertilizer. Further, sparsely placed, potted plants may not provide adequate coverage for a built environment.

Plant walls may provide more coverage for built environments. However, they also require significant maintenance. Surface temperature, light illumination, flow rate, water composition, and water level are just some of the important features of plant life and health. Currently, plant owners and maintainers must constantly monitor these variables and respond to the system when one or more of these features is not operating optimally.

A need exists for a self-maintaining, aesthetically pleasing device for growing plants in built environments.

SUMMARY OF THE INVENTION

These and other advantages and novel features of the present invention, as well as details of illustrated aspects thereof, will be more fully understood from the following description and the figures.

It is to be understood that both the preceding general description and the following detailed description describe various aspects and are intended to provide an overview or framework for understanding the nature and character of the claimed subject matter. The accompanying drawings are included to provide a further understanding of the various aspects and are incorporated into and constitute a part of this specification. The drawings illustrate the various aspects described herein, and together with the description serve to explain the principles and operations of the claimed subject matter.

Aspects of the present disclosure are directed to a vegetation wall system capable of monitoring at least one aspect in a vegetation wall system. By combining a set of sensors and a communication network, devices share information with one another improving their effectiveness and functionality.

One aspect, of the present disclosure is a vegetation wall system comprising a tank; a vegetation mounting unit with two portions, an upper portion, and a lower portion; at least one vegetation holding unit, media panel, or vegetation housing unit; a lighting unit releasably coupled to the upper portion of the vegetation mounting unit; a pump configured to feed water from the tank to the upper portion of the vegetation mounting unit; and a programmable logic control unit wherein the programmable logic control unit comprises at least one sensor configured to measure at least one aspect in a vegetation wall system and at least one control unit that is communicatively coupled to input and output units. In some aspects, further comprises a router. In a further aspect, the router is a wireless router, releasably attached to the lighting unit.

In one aspect of the vegetation wall system the at least one sensor is selected from the group consisting of: water level sensor or sensors; moisture level sensor or sensors; flow rate sensor or sensor; water composition sensor or sensors; temperature sensor or sensors; or light illumination sensor or sensors; and any combination thereof. In another aspect, the programmable logic control unit further comprises a transmitter configured to receive data from weather satellites, GPS, or NIST. In yet another aspect, the programmable logic control unit may monitor at least two or more aspects in a vegetation wall system individually or simultaneously.

In a further aspect, the vegetation wall system comprises at least two or more sensors. In another aspect, the vegetation wall system further comprises a router, at least two sensors, wherein one sensor is a liquid detection sensor and wherein one sensor is a flow sensor, and wherein the programmable logic control unit is configured to monitor the flow rate of water through an irrigation system of the vegetation wall system, the level of water in an tank of the vegetation wall system, the moisture level in at least one vegetation holding unit, media panel, or vegetation housing unit of the vegetation wall system, and/or the moisture level in the entire vegetation wall system.

Aspects of the present disclosure are also directed to methods of monitoring at least one aspect in a vegetation wall system.

One aspect is a method of monitoring the at least one aspect in the vegetation wall system the method comprising: measuring, by a sensor, a first component and a second component in the vegetation wall system; determining, by a processor, a change in the at least one aspect based on: the first component, the second component, and an amount of time between the measurement of the first component and the second component; determining whether the change in at least one aspect is outside a threshold range; and in response to determining the change in the at least one aspect is outside the threshold range, determining an anomalous condition exists.

In another aspect, the first component and second component are independently selected from the group consisting of the level of water in a tank of the vegetation wall system, flow rate of water through an irrigation system of the vegetation wall system, flow rate of water through at least one irrigation line of the vegetation wall system, moisture level in at least one vegetation holding unit, media panel, or vegetation housing unit of the vegetation wall system, moisture level of the entire vegetation wall system, and surface light intensity. In a further aspect, at least two or more aspects in the vegetation wall system may be monitored individually or simultaneously.

In one aspect, the sensor is selected from the group consisting of: a water level sensor or sensors; a moisture level sensor or sensors; a flow rate sensor or sensor; a water composition sensor or sensors; a temperature sensor or sensors; or a light illumination sensor or sensors; and any combination thereof.

In another aspect, the method further comprises generating an alert in response to determining that the anomalous condition exists. In a further aspect, the alert generated is selected from the group consisting of illuminating an alert light, sounding an alarm, activating a system response within the vegetation wall system, displaying a notification in a browser-based dashboard, sending an email to a user, sending a text message to a user, sending a push notification through an application to a mobile device, and displaying a notification through an application on a mobile device. In yet a further aspect, the system response is selected from the group consisting of adjusting the duration of time that the pump operates, disabling a tank, providing power to a solenoid valve on a water feed line to fill the tank, reducing the power to the pump to lower flow rate, increasing the power to the pump to raise flow rate, providing power to an actuator and injecting oxygen into the water, activating a fan to cool surface temperature, increasing heat intensity of a heat lamp to increase surface temperature, and adjusting the intensity of at least one light. In another aspect, the system response is remotely deployed and/or managed or automatically deployed.

In one aspect, the at least one aspect monitored in the vegetation wall system is the operation of a pump of the vegetation wall system, flow rate of water through an irrigation system of the vegetation wall system, flow rate of water through an irrigation line of the vegetation wall system, level of water in an tank of the vegetation wall system, moisture level in at least one vegetation holding unit, media panel, or vegetation housing unit of the vegetation wall system, moisture level of the entire vegetation wall system, overwatering of at least one vegetation holding unit, media panel, or vegetation housing unit of the vegetation wall system, overwatering of the entire vegetation wall system, under-watering of at least one vegetation holding unit, media panel, or vegetation housing unit of the vegetation wall system, or under-watering of the entire vegetation wall system.

In another aspect, the sensor is a liquid detection sensor or a flow sensor, the first component is selected from the group consisting of a first water level in the tank, a first moisture content of least one vegetation holding unit, media panel, or vegetation housing unit of the vegetation wall system, and a first moisture content of the entire vegetation wall system, and the second component is selected from the group consisting of a second water level in the tank, a second moisture content of least one vegetation holding unit, media panel, or vegetation housing unit of the vegetation wall system, and a second moisture content of the entire vegetation wall system.

In another aspect, the liquid detection sensor is selected from the group consisting of a level sensor, an ultrasonic level sensor, optical level switch, a capacitance level sensor, a microwave/radar sensor, a vibrating or tuning fork sensor, a conductive sensor, a resistance sensor, a float switch sensor, and a bubbler sensor. In yet another aspect, the flow sensor is selected from the group consisting of an orifice-plate flow sensor, a flow nozzle, a venture tube, a turbine flowmeter, a positive-displacement meter a rotameter, a vortex-shedding sensor, a fluid-oscillator meter, a jet-deflection meter, an ultrasonic meter, a magnetic flow sensor, a magnetic piston, a laser-doppler flow sensor, and a pitot tube.

In another aspect, the anomalous condition is selected from the group consisting of overwatering, under-watering, low tank level, the water in the tank falls to a predetermined level above a pump inlet, insufficient amount of water delivered to at least one vegetation holding unit, media panel, or vegetation housing unit of the vegetation wall system, insufficient amount of water delivered to the entire vegetation wall system, insufficient moisture content of at least one vegetation holding unit, media panel, or vegetation housing unit of the vegetation wall system, insufficient moisture content of the entire vegetation wall system, irrigation line failure, a flow rate above a specific, desired rate or range, and a flow rate below a specific, desired rate or range.

In another aspect, the at least one aspect monitored is selected from the group consisting of: the level of water in the tank of the vegetation wall system, the moisture content in at least one vegetation holding unit, media panel, or vegetation housing unit of the vegetation wall system, the moisture content of the entire vegetation wall system, underwatering of at least one vegetation holding unit, media panel, or vegetation housing unit of the vegetation wall system, underwatering of the entire vegetation wall system, flow rate of water through an irrigation system of the vegetation wall system, flow rate of water through an irrigation line of the vegetation wall system, and operation of the pump; the anomalous condition is selected from the group consisting of: irrigation line failure, insufficient amount of water delivered to at least one vegetation holding unit, media panel, or vegetation housing unit of the vegetation wall system, insufficient amount of water delivered to the entire vegetation wall system, insufficient moisture content of at least one vegetation holding unit, media panel, or vegetation housing unit of the vegetation wall system, and insufficient moisture content of the entire vegetation wall system, and the alert generated is selected from the group consisting of sounding an alarm, activating a system response within the vegetation wall system, displaying a notification in a browser-based dashboard, sending an email to a user, sending a text message to a user, sending a push notification through an application to a mobile device, and displaying a notification through an application on a mobile device, wherein the notification, email, or text directs a user to replace a pump or a timer, change the timer settings, fill the tank, replace or clean the irrigation line or the system response comprises adjusting the timer setting. In a further aspect, at least two aspects are monitored simultaneously.

In one aspect, the at least one aspect monitored is selected from the group consisting of: the level of water in the tank of the vegetation wall system, the moisture content in at least one vegetation holding unit, media panel, or vegetation housing unit of the vegetation wall system, the moisture content of the entire vegetation wall system, overwatering of at least one vegetation holding unit, media panel, or vegetation housing unit of the vegetation wall system, overwatering of the entire vegetation wall system, and operation of the pump; the anomalous condition is low-tank level or the water in the tank falls to a predetermined level above a pump inlet; and the alert generated is selected from the group consisting of sounding an alarm, activating a system response within the vegetation wall system, displaying a notification in a browser-based dashboard, sending an email to a user, sending a text message to a user, sending a push notification through an application to a mobile device, and displaying a notification through an application on a mobile device, wherein the notification, email, or text directs a user to replace a pump or timer, change the timer settings, or fill the tank or the system response comprises adjusting the duration of time that the pump operates or providing power to a solenoid valve on a water feed line to fill the tank. In a further aspect, at least two aspects are monitored simultaneously.

In another aspect, the at least one aspect monitored is selected from the group consisting of: flow rate of water through an irrigation system of the vegetation wall system, flow rate of water through an irrigation line of the vegetation wall system, and operation of the pump; the anomalous condition is a flow rate below a specific, desired rate or range or a flow rate above a specific, desired rate or range; and the alert generated is selected from the group consisting of sounding an alarm, activating a system response within the vegetation wall system, displaying a notification in a browser-based dashboard, sending an email to a user, sending a text message to a user, sending a push notification through an application to a mobile device, and displaying a notification through an application on a mobile device, wherein the notification, email, or text directs a user to replace a pump or a timer, change the timer settings, fill the tank, adjust the duration of time that the pump operates or the system response comprises adjusting the duration of time that a pump operates. In a further aspect, at least two aspects are monitored simultaneously.

In another aspect, the amount of time between measuring of the first component and the second component is dependent on the flow rate of the irrigation system.

In one aspect, the at least one aspect monitored in the vegetation wall system is surface light illumination of the vegetation wall system, the sensor is a surface light sensor, the first component is a first level of light illumination and the second component is a second level of light illumination and, the anomalous condition is that the surface light intensity is above a threshold level or below a threshold level. In another aspect, the method further comprises dimming or increasing the amount of light projected to the surface of the vegetation wall system in response to determining the anomalous condition exists. In another aspect, the light projected to the surface of the vegetation wall system further comprises a peripheral, integral, derivative loop. In a further aspect, each light is controlled by the peripheral, integral, derivative loop independently or each light is synchronized by the peripheral, integral, derivative loop. In yet another aspect, the light projected to the surface of the vegetation wall system comprises a manual or automatic adjustment.

DESCRIPTION OF THE DRAWINGS

The following is a description of the examples depicted in the accompanying drawings. The figures are not necessarily to scale, and certain features and certain views of the figures may be shown exaggerated in scale or in schematic in the interest of clarity or conciseness.

Figure 1:
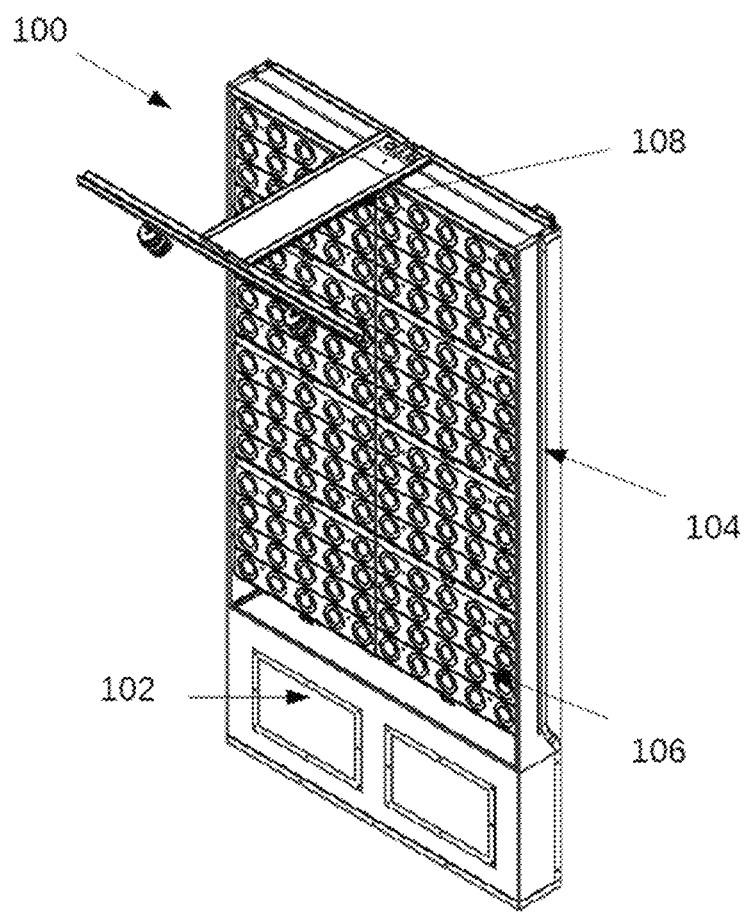
FIG. 1 depicts an aspect of a standalone vegetation wall.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION OF THE INVENTION

The U.S. provisional patent application Ser. No. 62/749,827 filed Oct. 24, 2018 is incorporated herein by reference.

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

In the following detailed description, specific details may be set forth in order to provide a thorough understanding of different aspects of the present disclosure. However, it will be clear to one skilled in the art when disclosed examples may be practiced without some or all of these specific details. For the sake of brevity, well-known features or processes may not be described in detail. In addition, like or identical reference numerals may be used to identify common or similar elements.

One or more specific aspects of the present disclosure will be described below. In an effort to provide a concise description of these aspects, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure.

When introducing elements of various aspects of the present disclosure, the articles "a," "an," "the," and "said" are intended to mean that there are one or more of the elements. The terms "comprising," "including," and "having" are intended to be inclusive and mean that there may be additional elements other than the listed elements.

FIG. 1 depicts one aspect of a standalone vegetation wall system 100. The vegetation wall 100 includes a tank cladding 102, a vegetation mounting unit 104, a vegetation holding unit, also known as a media panel or vegetation housing unit, 106, and a lighting unit or lighting fixture 108.

Figure 2:
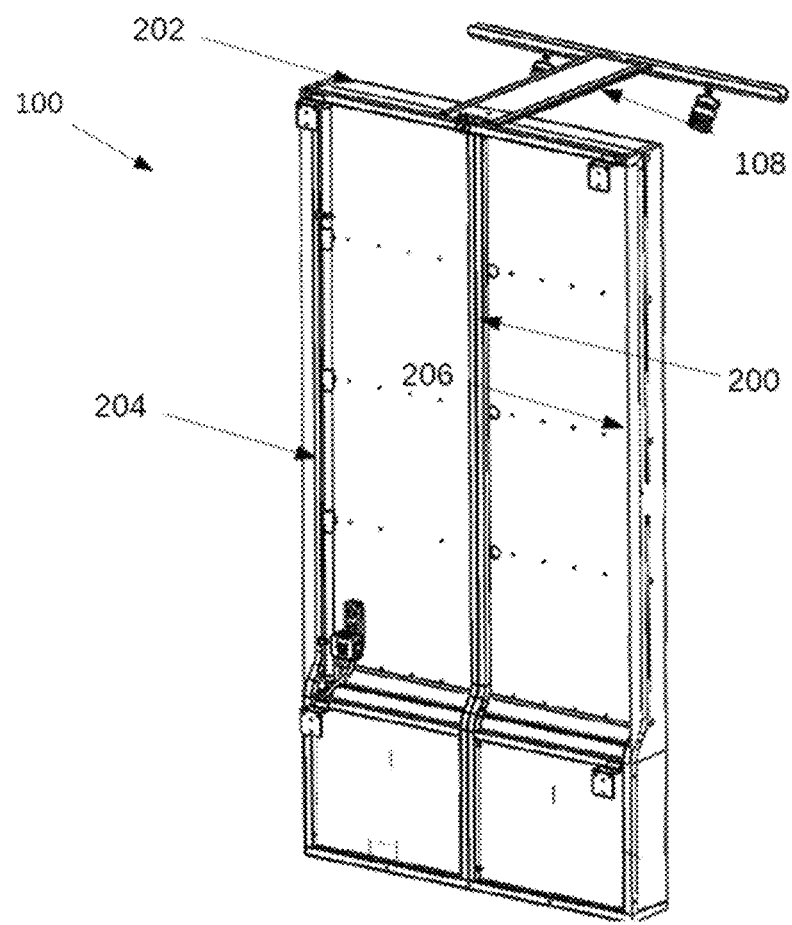
FIG. 2 depicts an aspect of a rear view of the vegetation wall.

FIG. 2 depicts a rear view of one aspect of a standalone vegetation wall system 100. The vegetation wall 100 includes a central support 200, top support 202, and side supports 204 and 206.

Figure 3:
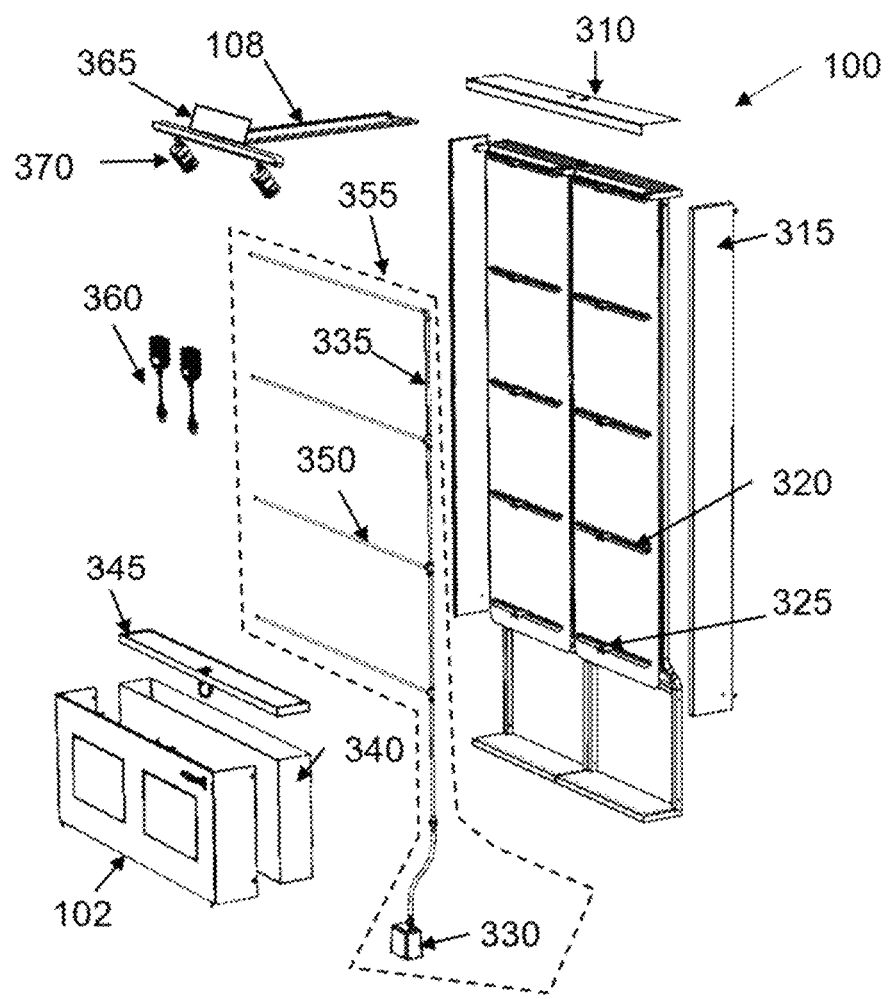
FIG. 3 depicts an aspect of an exploded view of a vegetation wall system.

FIG. 3 depicts an exploded view of a vegetation wall system 100. The vegetation wall system includes a top cladding 310 and side claddings 315. It further includes battens 320 and clips 325 capable of holding plant modules in place. Horizontal irrigation drip lines 350 are threaded through the battens 320 and vertical irrigation riser tubes 335 feed into the pump 330, collectively these elements make up the irrigation system 355. In some aspects, the pump 330 is an irrigation pump. The pump 330 is attached to the tank 340. In some aspects, the pump 330 is placed on the right side of the tank 340. Tank cladding 102 surrounds the tank 340 and a lid 345 covers the tank 340. The lid 345 may include a gutter and a filter. The filter may be a foam filter (for example, Poret®). The vegetation wall system 100 includes a light fixture 108. A wireless router 365 may be installed on top of the light fixture 108. In operation, a programmable logic control unit ("PLCU") or units 360 are plugged into the light fixture 108 or the pump 330 or both.

Figure 4:
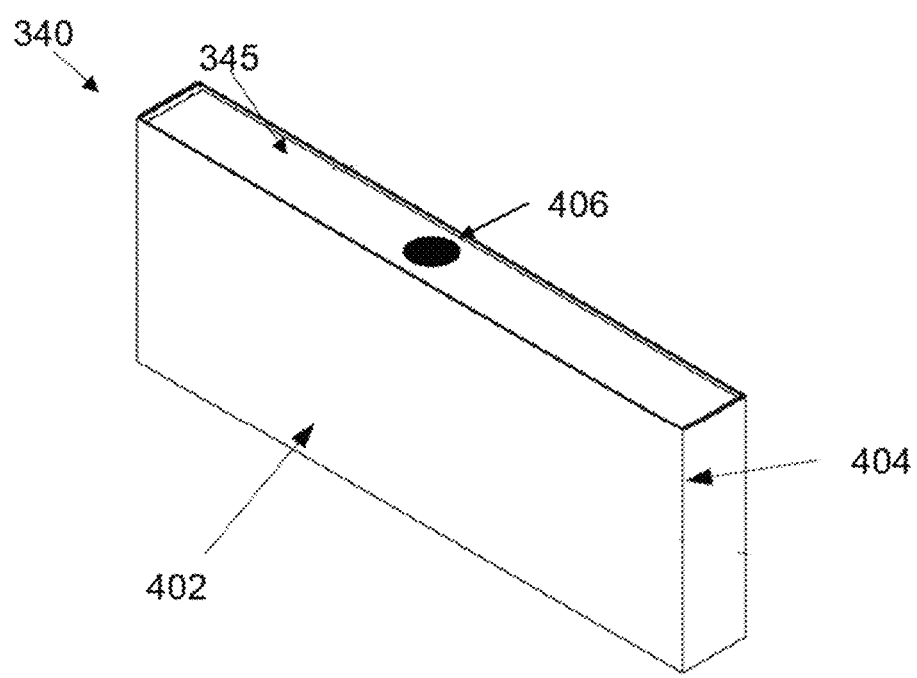
FIG. 4 depicts an aspect of a perspective view of the tank.

FIG. 4 depicts a perspective view of one aspect of a tank 340. The tank includes a front wall 402, side walls 404 and an opening 406 in the lid 345 of the tank to allow water to return into the tank 340.

Figure 5:
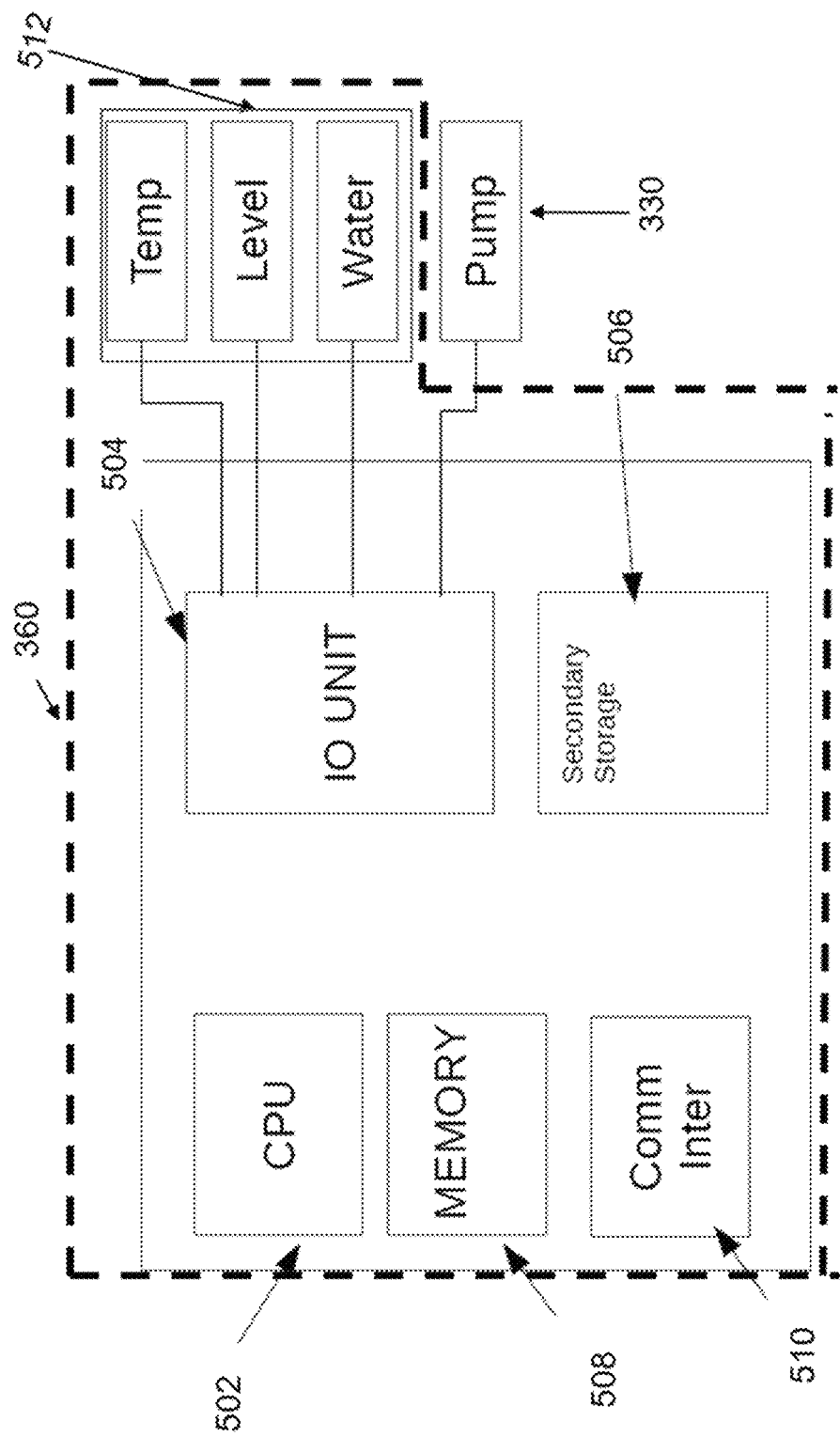
FIG. 5 depicts an aspect of a programmable logic control unit.

FIG. 5 depicts one aspect of a programmable logic control unit ("PLCU") 360 used to monitor and control various aspects of the vegetation wall system. The PLCU 360 includes a central processing unit ("CPU") 502, an input/output unit 504, secondary storage 506, memory 508, and a communications interface unit 510. A plurality of sensors 512 and control units are communicatively coupled to the input/output unit 504. The sensors 512 may include temperature sensors, liquid detection sensors, flow sensors, pressure sensors, or any other type of sensor. The control units may include relays, transducers, pulse width modulating units, or any other type of control unit. The communication interface unit 510 may be any known communication interface unit 510 that can communicate using known communication protocols, including BACnet, Echelon, TCP/IP, Ethernet, or any other communication protocol. In some aspects, the sensor 512 is a dual technology sensor. In other aspects, the sensor 512 is part of a wireless sensor network.

The vegetation wall system may be configured to or the PLCU 360 may be programmed to monitor various aspects of the vegetation wall system including the surface light illumination of the system, the moisture level in each vegetation holding unit, media panel, or vegetation housing unit, the flow rate of water through the system, the level of the tank, and any other monitored aspect. The PLCU 360 may comprise a timer. Further, the vegetation wall system may be configured to or PLCU 360 may be programmed to control various devices, including the pump 330 or the lighting 108, in response to the readings from at least one sensor. In some examples, the vegetation wall system may be configured to or the PLCU 360 may be programmed to control various devices in response to the readings from two or more sensors. As an illustrative example, a light measuring sensor may be mounted on the vegetation wall system to measure the illuminated intensity of the vegetation wall system. If the intensity exceeds a predetermined value, a light 370 may be dimmed to reduce the amount of light projected to the surface. The program may incorporate a peripheral, integral, derivative loop ("PID loop") to continue to dim the lighting to reduce the intensity. In one aspect, each light is controlled by the PID loop independently. In another aspect, each light is synchronized by the PID loop. The PLCU 360 may be configured to receive data from various transmitters, including weather satellites, global positioning satellites (GPS), or from the official National Institute of Standards and Technology (NIST) (time).

The vegetation wall system, using, for example, a processor, may monitor the level of water in the tank 340 using a level sensor, such as an ultrasonic level sensor. If the level of the tank 340 drops below a predetermined threshold, the vegetation wall system may provide an alert or a response such as providing power to a solenoid valve on a water feed line to fill the tank 340. In one example, the tank 340 may hold 18 inches of water, and 0-4 inches of water may be outside the threshold range. In another example, the tank 340 may hold 4 inches of water, and 0-2 inches of water may be outside the threshold range. In another example, a user may specify a unique range based on a predetermined amount of water above the inlet of the pump.

As another illustrative example, if the level of the tank 340 drops below a predetermined threshold, the vegetation wall system may trigger an alert, for example, an electronic message to a service technician to fill the tank 340. As another illustrative example, the vegetation wall system using, for example, a processor may monitor the moisture level of at least one vegetation mounting unit or media panel 106 to determine if adequate moisture is getting to the plants. If the moisture level drops below a predetermined level, the PLCU 360 may provide power to the pump 330 to provide water to the vegetation wall system.

Figure 6:
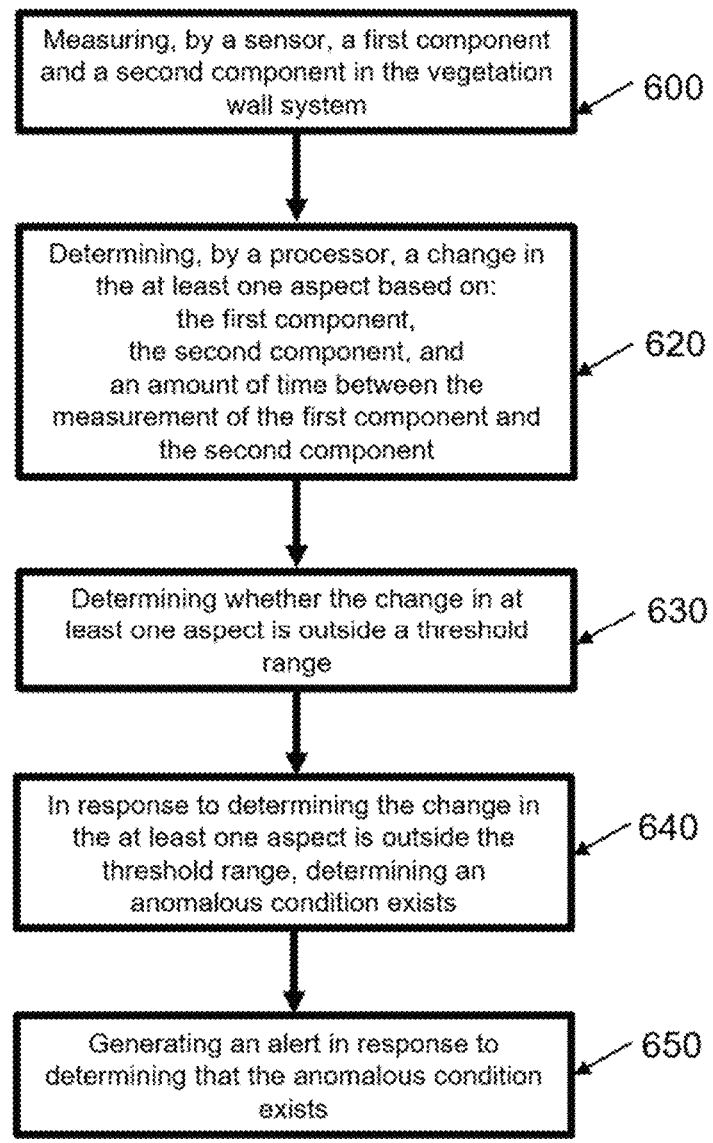
FIG. 6 depicts a flow diagram of a method of monitoring at least one aspect in the vegetation wall system.

FIG. 6 depicts a method of monitoring at least one aspect in the vegetation wall system 100. First, a sensor 512 of the vegetation wall system 100 is configured to measure a first component and a second component in the vegetation wall system 600. Second, a processor may determine a change in the at least one aspect based on the first component, the second component, and the amount of time between the measurement of the first component and the second component 620. Third, the processor may determine whether the change in at least one aspect is outside a threshold range 630. In response to determining that the change in the at least one aspect is outside the threshold range, the processor may determine that an anomalous condition exists 640. Finally, the processor may generate an alert in response to determining that an anomalous condition exists 650.

Figure 7:
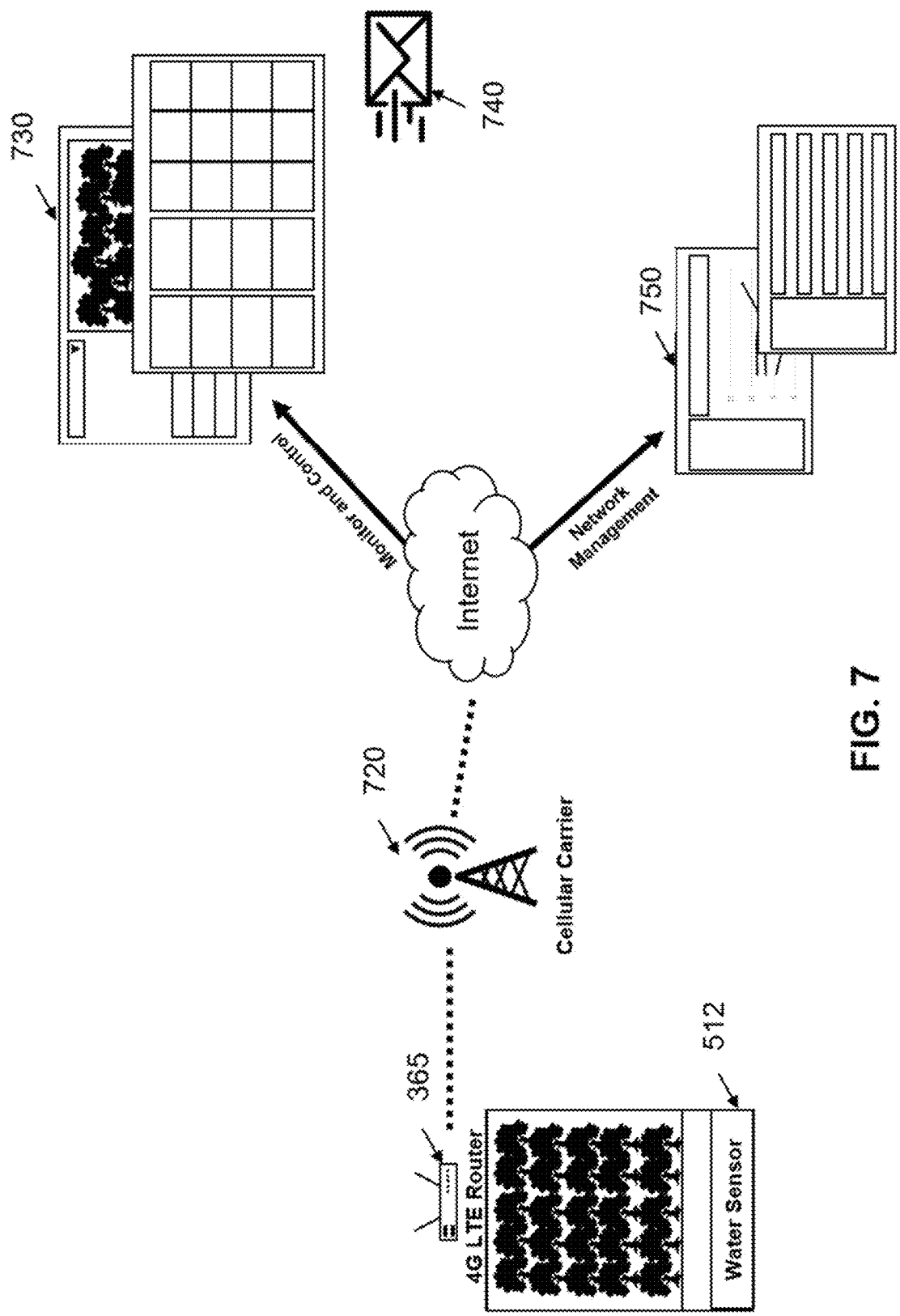
FIG. 7 depicts an aspect of an irrigation sensor system.

By way of even more specific example, FIG. 7 illustrates a method of monitoring changes in water level in a vegetation wall system using a sensor 512. Specifically, monitoring for (i) overwatering, (ii) underwatering and/or (iii) low water levels in the tank. A wireless router 365 transmits sensor data to an internet of things (I) software-as-a-service (SaaS) solution platform 730 via a secure cellular network 720. The advantage of this system is that no WiFi access is required. This feature can prove useful as the vegetation wall system may be placed in areas where WiFi is unavailable. A wireless network data provider provides redundant cellular connectivity to the wireless router 365. The IoT-SaaS platform 730 displays irrigation system state along with key product, customer, and maintenance provider information. The IoT-SaaS platform 730 also generates an alert notifying a user (for example, via email 740) if an anomalous condition is detected so it may be triaged and resolved. The wireless router allows remote monitoring, provisioning, and updating of the router network and router-based software applications 750.

In some examples, the vegetation wall system 100 comprises sprinklers or a drip line that are/is configured to run for not more than a minute. In these instances, to detect for overwatering, the sensors 512 detect a first water level within the tank 340 and detect a second level within the tank 340 at least 6 minutes after detecting the first level, alternatively at least 5 minutes, alternatively at least 4 minutes, alternatively at least 3 minutes, alternatively at least 2 minutes, or alternatively at least 1 minute. However, the amount of time between the detection of the first water level and the second water level may also be dependent on the flow rate of the irrigation system 355. In these examples, if the sensors 512 detect overwatering, in addition to generating an alert, the vegetation wall system using, for example, the PLCU 360 may reduce the time that the pump 330 operates.

In some examples, service technicians or other users may accidentally disable or reset the sprinklers or drip line. This may result in underwatering of the vegetation wall system 100. In these instances, to detect for underwatering, the sensors 512 detect a first water level within the tank 340 and detect a second level within the tank 340 at least 12 hours after detecting the first level, alternatively at least 24 hours, alternatively at least 36 hours, alternatively at least 48 hours, alternatively at least 60 hours, or alternatively at least 72 hours. In these examples, if the sensors 512 detect underwatering, in addition to generating an alert, the vegetation wall system using, for example, the PLCU 360 may increase the time the pump operates.

In some examples, the water in the tank 340 of the vegetation wall system 100 may be low. This could be, for example, due to environmental conditions or overwatering of the vegetation wall system 100. In some examples of the vegetation wall system 100, the tank 340 may hold 18 inches of water and 0-4 inches of water may be outside the threshold range. In another example, the tank 340 may hold 4 inches of water and 0-2 inches of water may be outside the threshold range. In another example, less than half of the volume of the tank 340 may be outside the threshold range. In another example, a user may specify a unique range based on a predetermined amount of water above the inlet of the pump. In these examples, if the sensors 512 detect a low tank level, in addition to generating an alert, the vegetation wall system using, for example, the PLCU 360 may reduce the time that the pump 330 operates.

Monitoring levels of the water in the tank 340 may also provide a user information regarding the operation of the pump 330 or the flow rate of the irrigation system 355. As such, in some examples, sensors 512 are configured to monitor the specific flow rates at predetermined times. In these examples, in addition to generating an alert, if a processor determines the flow rate is lower than a specified threshold value the processor may increase the time the pump 330 operates. However, if the processor determines that the flow rate is higher than a specified threshold value, the processor may decrease the time the pump 330 operates or disable the pump 330.

The vegetation wall system may be configured to monitor and remedy multiple vegetation wall system aspects simultaneously. It may be configured to monitor the operation of the pump of the vegetation wall system, the flow rate of water through an irrigation system of the vegetation wall system, and the moisture level in at least one vegetation holding unit, media panel, or vegetation housing unit of the vegetation wall system simultaneously or independently. Potential anomalous conditions related to these aspects include overwatering, under-watering, low tank level, the water in the tank falls to a predetermined level above a pump inlet, insufficient amount of water delivered to at least one vegetation holding unit, media panel, or vegetation housing unit of the vegetation wall system, insufficient amount of water delivered to the entire vegetation wall system, insufficient moisture content of at least one vegetation holding unit, media panel, or vegetation housing unit of the vegetation wall system, insufficient moisture content of the entire vegetation wall system, irrigation line failure, a flow rate above a specific, desired rate or range, and a flow rate below a specific, desired rate or range. The vegetation wall system then generates an appropriate alert or system response to remedy the anomalous condition or conditions. For example, in this configuration, the vegetation wall system would include a liquid detection sensor (or sensors) and a flow sensor (or sensors). The vegetation wall system may also be configured to monitor and remedy individual vegetation holding unit, media panel, or vegetation housing unit 106 of the vegetation wall system 100 independently of each other or simultaneously.

Figure 8:
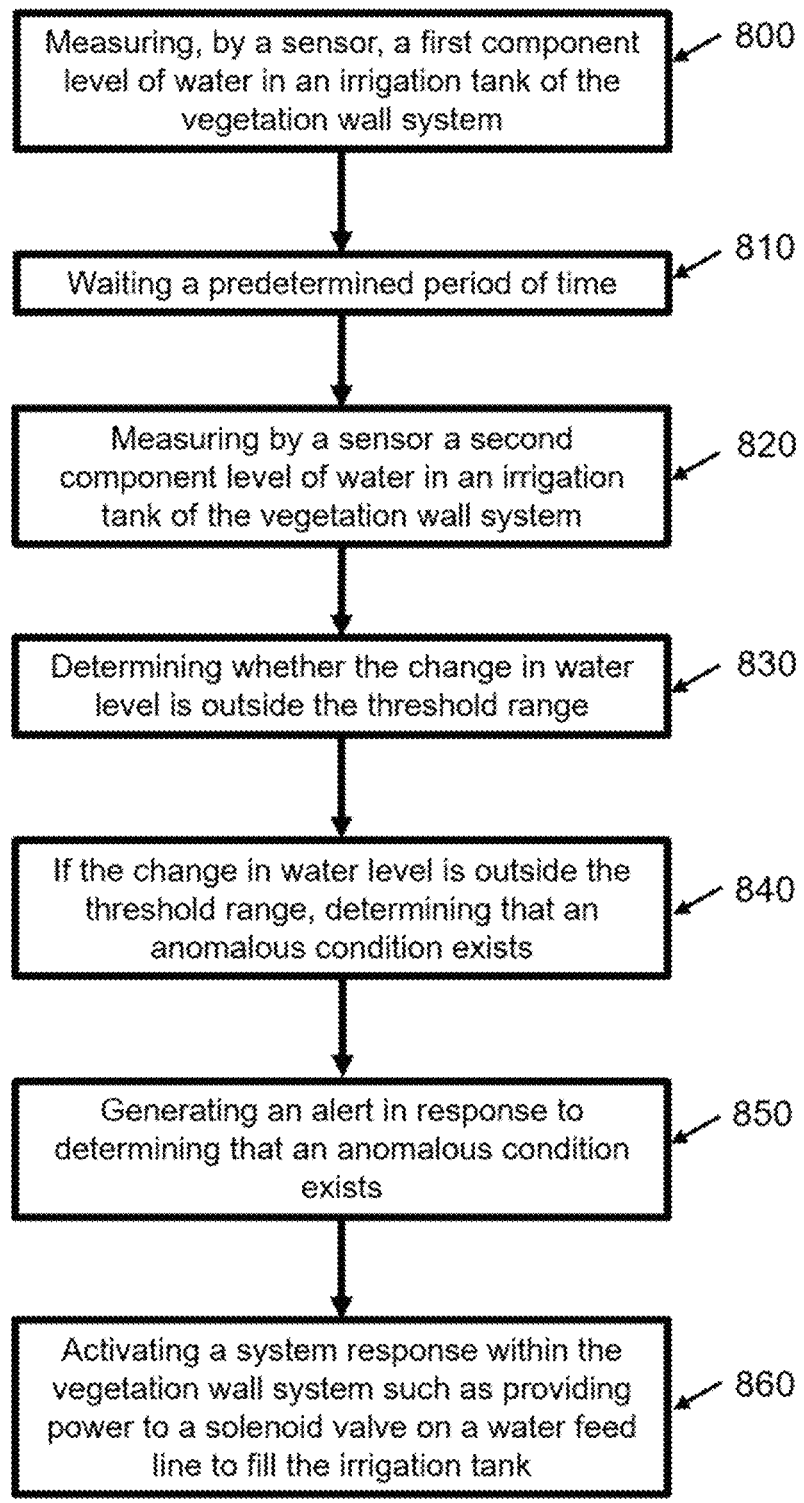
FIG. 8 depicts a flow diagram of a method of monitoring the level of water in an irrigation tank of the vegetation wall system.

FIG. 8 depicts a method of monitoring the water level in a tank 340 of the vegetation wall system 100. First, a sensor 512 of the vegetation wall system 100 may measure a first component level of water in the vegetation wall system 800. Second, a processor may direct the sensor 512 to wait a predetermined period of time 810. Third, the sensor 512 may measure a second component level of water in a tank 340 of the vegetation wall system 820. Fourth, the processor may determine whether the change in water level is outside the threshold range 830. If the change in water level is outside the threshold range, the processor may determine that an anomalous condition exists 840. Fifth, the processor may generate an alert in response to determining that an anomalous condition exists 850. Finally, the processor may activate a system response within the vegetation wall system 100 that is remotely deployed and/or managed or automatically deployed. This includes, but is not limited to, providing power to a solenoid valve on a water feed line to fill the tank 860. In this aspect, no human intervention is necessary, as the processor watches, monitors, and adjusts the anomalous condition. However, in another aspect, instead of activating a system response within the vegetation wall system 100, an alert may be generated directing a technician to fill the tank.

Figure 9:
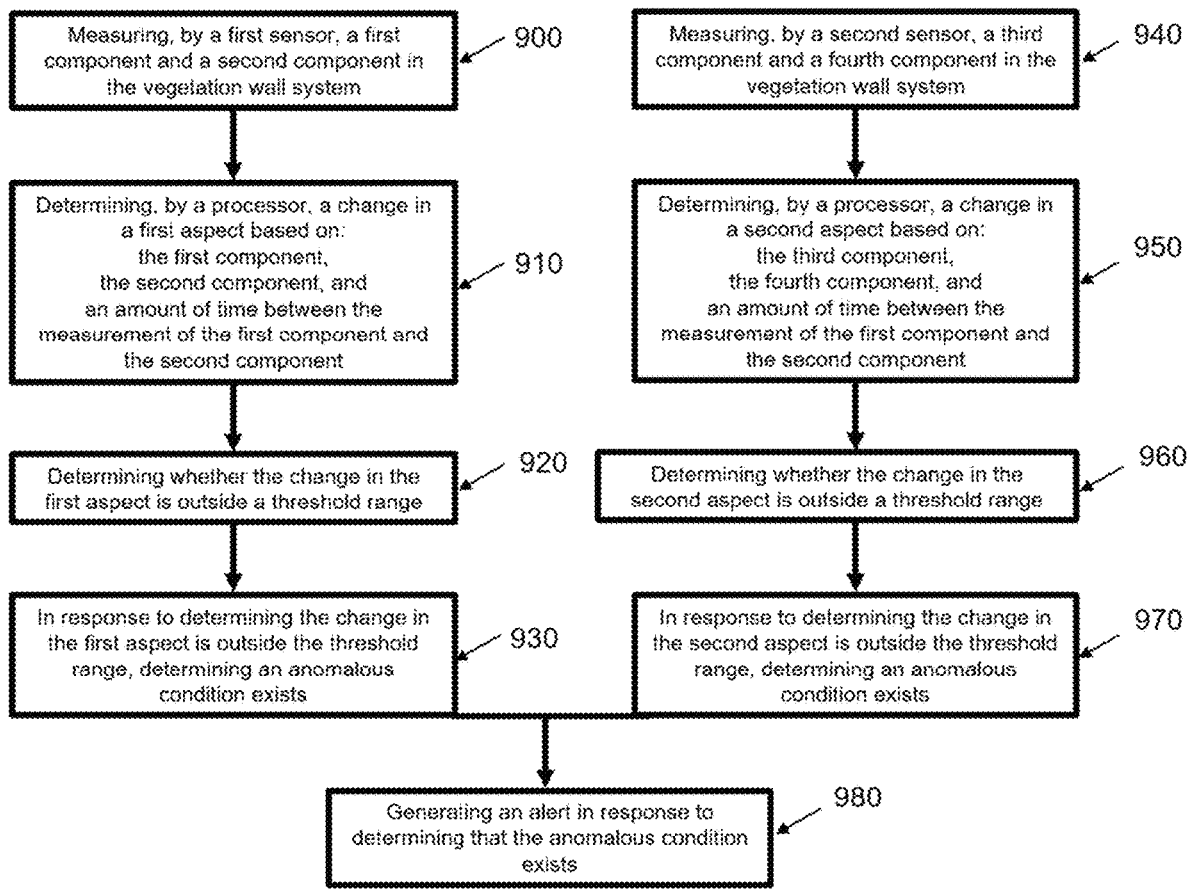
FIG. 9 depicts a flow diagram of a method of monitoring two aspects of the vegetation wall system simultaneously.

FIG. 9 depicts a method of monitoring two aspects of a vegetation wall system simultaneously. A first sensor of the vegetation wall system 100 is configured to measure a first component and a second component in the vegetation wall system 900. Then, a processor may determine a change in a first aspect based on the first component, the second component, and the amount of time between the measurement of the first component and the second component 910. Then, the processor may determine whether the change in the first aspect is outside a threshold range 920. In response to determining that the change in the first aspect is outside the threshold range, the processor may determine that an anomalous condition exists 930. At the same time, a second sensor of the vegetation wall system 100 is configured to measure a third component and a fourth component in the vegetation wall system 940. Then, the processor may determine a change in the second aspect based on the third component, the fourth component, and the amount of time between the measurement of the third component and the fourth component 950. The processor may determine whether the change in the second aspect is outside a threshold range 960. In response to determining that the change in the second aspect is outside the threshold range, the processor may determine that an anomalous condition exists 970. Finally, the processor may generate an alert in response to determining that an anomalous condition exists for either the first aspect, second aspect, or both aspects 980.

As an example, the vegetation wall system may monitor for insufficient water, a system-wide condition that results in the entire vegetation wall system getting too little water. Sensors 512 may configured to monitor the level of water in the tank, and if the water level is not being lowered at the appropriate rate, then the processor may determine that an anomalous condition exists. The processor may then generate an alert in response to determining that the anomalous condition exists which includes providing an alert to replace a pump or timer, change the timer settings, or the system response comprises adjusting the timer setting.

In another example, the vegetation wall system may monitor for irrigation line failure, a condition that is specific to an irrigation line that results in only a portion of the wall receiving too little water. This could be due to a clog in the irrigation line or a faulty irrigation system, sensors 512 may be configured to monitor the moisture content of a media panel, vegetation holding unit, or vegetation housing unit in a specific location. If the moisture measurements do not meet a threshold value the processor may determine that an anomalous condition exists. The processor may then generate an alert in response to determining that the anomalous condition exists which includes providing an alert to replace a pump or a timer, change the timer settings, fill the tank, replace or clean the irrigation line or the system response comprises adjusting the timer setting.

In some examples, the vegetation wall system can monitor for both insufficient water and irrigation line failure simultaneously.

In an example, the vegetation wall system is configured to monitor the water level of one or more vegetation panel units 106 via a sensor 512, and the irrigation system (i.e., by measuring the flow rate and tank levels) via a sensor 512, simultaneously. If the water level of the vegetation panels units is found to be below a minimum threshold and the irrigation system is determined to be running properly via the sensors 512, the vegetation wall system will generate an alert, for example notifying a technician that there may be a clog in the water line.

In another example, if the irrigation system is running properly, but the water level of one or more of the vegetation panel units 106 is found to be above a specified range, the processor may generate an alert, for example notifying a technician to reprogram the timer(s) for the irrigation system, or the vegetation wall system may remedy the anomalous condition without human interaction by changing the length of time the timers are on within the system 355.

In another example, the vegetation wall system may be configured to monitor the water level of the tank 340 and the flow rate of water through the irrigation system 355 simultaneously. If the flow rate is within a normal specified range and the tank level is above a normal, specified range, the vegetation wall system will generate an alert, for example notifying a technician that the opening 406 on the lid may be clogged.

In another example, the vegetation wall system may be configured to monitor the water level of the tank 340 and the flow rate of water through the irrigation system 355 simultaneously. If the flow rate is below a normal specified range and/or the tank level is unchanging, the vegetation wall system will generate an alert, for example notifying a technician that the pump 330 may be broken or are in need of replacement.

In another example, if the vegetation wall system stops receiving a transmission from any of the one or more of the sensors 512 within a specified period of time, the vegetation wall system will generate an alert, for example notifying a technician that the sensors may be broken or are in need of replacement.

In addition to monitoring the level of water in the tank of the vegetation wall system, monitoring the operation of the pump of the vegetation wall system, monitoring the flow rate of water through an irrigation system of the vegetation wall system, or monitoring the moisture level in at least one vegetation holding unit, media panel, or vegetation housing unit of the vegetation wall system, another aspect of the method may include monitoring the surface light intensity of the vegetation wall system, monitoring the composition of the water in an tank of the vegetation wall system, and monitoring the surface temperature of at least one location on the vegetation wall system.

Monitoring the composition of water may include monitoring the level of chemicals, elements, nutrients, anions, or cations in the water of the tank 340 of the vegetation wall system 100. The first and second components may be specified levels of a given chemical, element, nutrient, anion, or cation, and an anomalous condition may be the level of that chemical, element, nutrient, anion, or cation in the water above or below a threshold amount. In one example, the first and second components may be levels of chlorine. In another example, they may be levels of dissolved oxygen. The vegetation wall system may be configured to monitor the composition of water that may include different types of sensors such as nutrient sensors capable of measuring different plant nutrients, including those found the fertilizers, such as nitrogen, phosphorus, potassium, calcium, magnesium, sulfur, boron, manganese, iron, zinc, molybdenum, copper, dissolved oxygen and/or chlorine, total organic carbon sensor, turbidity sensor, conductivity sensor, pH sensor, and/or oxygen-reduction potential sensor. The sensor may monitor the system for anomalous conditions such as ineffectively low levels of such nutrients, or dangerously high levels of such nutrients and the vegetation wall system may generate an appropriate response to remedy the anomalous condition or notify a technician.

Monitoring of the surface temperature includes a method where the first and second components may be the surface temperature of a specific location on the vegetation wall system 100. In this aspect, the sensor 512 is a temperature sensor, the first component is a first temperature and the second component is a second temperature and the anomalous condition is that the temperature is above a threshold level or below a threshold level. The method may also be used to monitor the surface light illumination of the vegetation wall system 100. The sensor 512 may be a surface light sensor, and the first component may be a first level of light illumination and the second component may be a second level of light illumination. In response to determining that an anomalous condition exists for either aspect, the system may dim or increase the amount of light projected to the surface of the system. The vegetation wall system may also generate an alert response that turns the lights on (or off) for a shorter or longer period of time to remedy the anomalous condition. In other examples, the vegetation wall system will generate an alert notifying a technician to manually turn the lights on or off. If one or more of the lights are faulty or have burned out, the system will generate an alert notifying a technician to replace the light or lights.

In the present disclosure, the use of the singular includes the plural except where specifically indicated.

The presently described technology is now described in such full, clear, concise, and exact terms as to enable any person skilled in the art to which it pertains to practice the same. It is to be understood that the foregoing described preferred aspects of the technology and that modification may be made therein without departing from the spirit or scope of the invention as set forth in the appended claims. The scope of the following claims is to be accorded the broadest interpretation to encompass all such modifications and equivalent structures and functions. Therefore, it is intended that the application not be limited to the particular aspects disclosed, but that the application will include all aspects falling within the scope of the appended claims.

In accordance with the provisions of the patent statutes, the invention has been described in what is considered to represent its preferred embodiment. However, it should be noted that the invention can be practiced otherwise than as specifically illustrated and described without departing from its spirit or scope.

The invention claimed is:

1. A vegetation wall system comprising:
an irrigation tank;
a vegetation mounting unit;
a vegetation holding unit mounted on the vegetation mounting unit;
a pump configured to feed water from the irrigation tank to the vegetation holding unit;
a programmable logic control unit including a central processing unit, a first sensor and a second sensor; and
wherein the central processing unit monitors a first aspect and a second aspect in the vegetation wall system by,
measuring, by the first sensor, a component of the first aspect as a first component measurement,
waiting a first predetermined period of time and then measuring, by the first sensor, the component of the first aspect as a second component measurement,
determining, by the central processing unit, a first change in the first aspect based on the first component measurement, the second component measurement, and the first predetermined period of time between the first and second component measurements,
determining whether the first change is outside a first threshold range,
in response to determining that the first change is outside the first threshold range, determining that a first anomalous condition exists,
measuring, by the second sensor, a component of the second aspect as a third component measurement,
waiting a second predetermined period of time and then measuring, by the second sensor, the component of the second aspect as a fourth component measurement,
determining, by the central processing unit, a second change in the second aspect based on the third component measurement, the fourth component measurement, and the second predetermined of time between the third and fourth component measurements,
determining whether the second change is outside a second threshold range,
in response to determining that the second change is outside the second threshold range, determining that a second anomalous condition exists, and
generating an alert in response to determining that at least one of the first and second anomalous conditions exist.

2. The vegetation wall system according to claim 1, including a wireless router transmitting data generated by the first and second sensors to an Internet of Things Software as a Service platform.

3. The vegetation wall system according to claim 1, wherein the first and second sensors are selected from a group consisting of: a water level sensor; a moisture level sensor; a flow rate sensor; a water composition sensor; a temperature sensor; and a light illumination sensor.

4. The vegetation wall system according to claim 1, wherein the programmable logic control unit further comprises a communications interface configured to receive data from weather satellites, GPS and/or NIST.

5. The vegetation wall system according to claim 1, wherein the first sensor is a liquid detection sensor and wherein the second sensor is a flow sensor, and wherein the central processing unit monitors at least two of a flow rate of water through an irrigation system of the vegetation wall system, a level of water in the irrigation tank, a moisture level in the vegetation holding unit, and a moisture level in the entire vegetation wall system using at least one of the first and second sensors.

6. The vegetation wall system according to claim 1 wherein the central processing unit responds to the alert by at least one of: adjusting a duration of time that the pump operates; disabling the irrigation tank; providing power to a solenoid valve on a water feed line to fill the irrigation tank; reducing power to the pump to lower a flow rate from the irrigation tank; increasing power to the pump to raise the flow rate from the irrigation tank; providing power to an actuator to inject oxygen into the water in the irrigation tank; activating a fan to cool a surface temperature of the water in the irrigation tank; increasing heat intensity of a heat lamp to increase a surface temperature of the water in the irrigation tank; and adjusting an intensity of a light in the system.

* * * * *